United States Patent [19]
Geliebter et al.

[11] Patent Number: 6,150,338
[45] Date of Patent: Nov. 21, 2000

[54] GENE THERAPY FOR ALLEVIATING ERECTILE DYSFUNCTION

[75] Inventors: Jan Geliebter, Brooklyn; Arnold Melman, Ardsley; George J. Christ, Smithtown; Jamil Rehman, Bronx, all of N.Y.

[73] Assignee: Albert Einstein College of Medicine of Yeshiva University, Bronx, N.Y.

[21] Appl. No.: 08/799,144

[22] Filed: Feb. 13, 1997

(Under 37 CFR 1.47)

[51] Int. Cl.$^7$ .......................... A61K 48/00; C12N 15/85; C07H 21/04
[52] U.S. Cl. ......................... 514/44; 435/325; 435/366; 536/23.1
[58] Field of Search .......................... 514/44, 645; 435/6, 435/320.1, 325, 366; 536/24.5, 23.1

[56] References Cited

U.S. PATENT DOCUMENTS

| | | | |
|---|---|---|---|
| 5,214,030 | 5/1993 | Stief | 374/12 |
| 5,219,748 | 6/1993 | Yoshitaka et al. | 435/194 |
| 5,324,651 | 6/1994 | Ono et al. | 435/194 |
| 5,594,032 | 1/1997 | Gonzalez-Cadavid et al. | 514/645 |

OTHER PUBLICATIONS

Christ et al., Molecular studies of human corporal smooth muscle: implications for the understanding, diagnosis, and treatment of erectile dysfunction, Mol. Urol. vol. 1 (1), pp. 45–54, 1997.

Wegner et al., Nitric oxide donor, linsidomine chlorhydrate (SIN–1), in the diagnosis and treatment of erectile dysfunction: critical appraisal and review of the literature, Int. Urol. Nephrol., vol. 27 (5), pp. 621–628, 1995.

George J. Christ, Ph.D., The Penis as a Vascular Organ. The Importance of Corporal Smooth Muscle Tone in the Control of Erection, Urol. Clin. North Am., vol. 22(4), pp 727–745, Nov. 1995.

Lerner, et al., A Review of Erectile Dysfunction: New insights and more questions, The Journal of Urology, vol. 149, pp 1246–1255, May 1993.

Christ, et al., Characterization of K Currents in Cultured Human corporal Smooth Muscle Cells, Journal of Andrology, vol. 14(5), pp. 319–328, Sep./Oct. 1993.

G.J. Christ, The "Syncytial Tissue Triad": A model for understanding how gap junctions participate in the local control of penile erection, World J. of Urology, vol. 15, pp. 36–44, 1997.

Christ, et al., The Role of Gap Junctions and Ion Channels in the Modulation of Electrical and Chemical Signals in Human Corpus Cavernosus Smooth Muscle, Int. J. Impotence Res. (1993) pp 577–96.

Fan, et al., An Analysis of the Maxi–K+($K_{Ca}$) Channel in Cultured Human Corporal Smooth Muscle Cells, The Journal of Urology, vol. 153, pp. 818–825, Mar. 1995.

Nabel, et al., Site–specific gene expression in vivo by direct gene expression into the arterial wall, Science, vol. 249:1285–8 (1990).

McCobb, et al., Human calcium–activated potassium channel gene expressed in vascular smooth muscle, Am. J. Physiol., vol. 269: H767–77 (1995).

*Primary Examiner*—George C. Elliott
*Assistant Examiner*—Andrew Wang
*Attorney, Agent, or Firm*—Amster, Rothstein & Bernstein

[57] ABSTRACT

The present invention is directed towards gene therapy for erectile dysfunction through delivery and expression of a recombinant vector containing a DNA sequence encoding a protein involved in the regulation of smooth muscle tone into a smooth muscle cell. Also provided by the present invention is a method of inducing penile erection in a subject comprising the introduction and expression of a DNA sequence encoding a protein involved in the regulation of smooth muscle tone into a sufficient number of cells of the subject to induce penile erection in the subject. The present invention also provides a recombinant vector comprising the DNA of or corresponding to at least a portion of the genome of a virus, which portion is capable of directing the expression of a DNA sequence, and DNA encoding a protein involved in the regulation of smooth muscle tone operably linked to the viral DNA and capable of being expressed as a functional gene product in the target cell. Also provided by the present invention is a smooth muscle cell which expresses a gene encoding a protein involved in the regulation of smooth muscle tone.

9 Claims, 5 Drawing Sheets

GENE THERAPY FOR ALLEVIATING ERECTILE DYSFUNCTION

BACKGROUND OF THE INVENTION

Erectile dysfunction is a common illness that is estimated to affect 10 to 30 million men in the United States (Feldman, et al. *Journal of Clinical Epidemiology* 47.5 (1994) 457–67; Anonymous, *International Journal of Impotence Research* 5.4 (1993) 181–284). Among the primary disease-related causes of erectile dysfunction are atherosclerosis, diabetes, aging, hypertension and antihypertensive medication, chronic renal disease, pelvic surgery and radiation therapy, and psychological anxiety (Feldman, et al. *Journal of Clinical Epidemiology* 47.5 (1994) 457–67). Direct cures for the vascular ravages of these manifold and multifaceted disease states are unlikely to occur in the near future, and thus, the last decade has witnessed the development of several treatment modalities to directly restore diminished erectile capacity. However, all currently available therapies are either non-specific (hormonal therapy), of limited overall success (e.g., vacuum erection devices), invasive (e.g., intracorporal injection therapy) or non-reversible and expensive (e.g., penile prosthetic implant surgery). Despite these therapeutic limitations the recent FDA approval of Caverject (prostaglandin $E_1$) for the intracavernous treatment of erectile dysfunction represents a major step forward. In essence, this act of the Federal Government has resulted in both the formal recognition of the medical nature of the problem, and furthermore, legitimized its clinical treatment.

Recent changes in contemporary cultural patterns in the United States have allowed for a free and more open public discussion of sex and sexual dysfunction. This cultural trend has both highlighted the magnitude of the problem, and simultaneously emphasized the need for improved clinical treatment of erectile dysfunction. The recent deluge of advertising and media activity related to the discussion and treatment of the problem has made men, and their sexual partners more aware that erectile dysfunction is a common problem with legitimate (federally approved) clinical treatments available. This combination of events will continue to promote even larger numbers of men to seek treatment for impotence from their physicians during the next decade. There is thus a need for a better understanding the impact of age and disease on human erection through the study of the function of the corporal and arterial smooth muscle at the whole tissue, cellular, and most recently at the subcellular level. Also needed is a research strategy that will enable the direct translation of the results of laboratory work to the clinical environment, ensuring that new treatments for organic erectile dysfunction will be more cost effective, of greater efficacy and with fewer side effects.

Studies have documented that altered corporal smooth muscle tone, resulting in either heightened contractility or impaired relaxation, is a proximal cause of erectile dysfunction in a large proportion of impotent men. These studies have further indicated that complete relaxation of the corporal smooth muscle is both a necessary and sufficient condition to restore erectile potency, unless severe arterial disease or congenital structural abnormalities exist; the latter is true in a minority of patients. The FDA approval of the intracavernous injection of the smooth muscle relaxant $PGE_1$ verifies the validity of this supposition.

As described above, the critical role played by the corporal smooth muscle cells in erectile function makes them a excellent target for molecular intervention in the treatment of erectile dysfunction. Previous efforts have focused on techniques for gene transfer into vascular smooth muscle cells as a basis for the potential therapy of several cardiovascular diseases. Among these are atherosclerosis, vasculitis and restenosis after balloon angioplasty. These initial studies have provided important information on the efficiency and persistence of gene transfer methods in smooth muscle cells (Finkel, et al. *FASEB Journal* 9 (1995) 843–51).

Thus, because erectile dysfunction is largely caused by altered smooth muscle tone, a method of gene therapy which targets the genes involved in the alteration of smooth muscle tone is extremely desirable. Further, of critical importance with respect to all in vivo gene therapy approaches is the percentage of target cells that must be affected, and the relative efficiency of affecting only the desired cell type(s) to see a physiologically relevant therapeutic effect. Accordingly, there is a need for a method of gene therapy wherein only a small number of cells would need to be genetically modified to affect global changes in tissue function. Finally, a successful method of gene therapy for alleviating erectile dysfunction is in great demand as it would be a preferred alternative to currently used methods.

SUMMARY OF THE INVENTION

The present invention is directed towards gene therapy for erectile dysfunction through delivery and expression of a recombinant vector containing a DNA sequence encoding a protein involved in the regulation of smooth muscle tone into a smooth muscle cell.

The present invention specifically provides for a method of gene therapy wherein the DNA sequence that encoding a protein that is involved in the regulation of smooth muscle cells encodes a protein that regulates corporal smooth muscle tone in a corporal smooth muscle cell by modulating vasorelaxation. These proteins will enhance corporal smooth muscle relaxation resulting in a more easily attained erection. Also contemplated is a method of gene therapy wherein the DNA sequence encodes a protein that inhibits vasoconstriction of a smooth muscle.

Also provided by the present invention is a method of inducing penile erection in a subject comprising the introduction and expression of a DNA sequence encoding a protein involved in the regulation of corporal smooth muscle tone into a sufficient number of cells of a subject to induce penile erection in the subject. In the preferred embodiment, the method of gene therapy of present invention is used to alleviate erectile dysfunction.

The present invention also provides a recombinant vector comprising the DNA of or corresponding to at least a portion of the genome of a virus, which portion is capable of directing expression of a DNA sequence, and DNA encoding a protein involved in the regulation of corporal smooth muscle tone operably linked to the viral DNA and capable of being expressed as a functional gene product in the target cell.

The present invention additionally provides for a smooth muscle cell, such as a corporal or arterial smooth muscle cell, that encodes a protein involved in the regulation of smooth muscle tone.

Additional objects of the invention will be apparent from the description which follows.

BRIEF DESCRIPTION OF THE FIGURES

FIG. 1.

FIG. 2: FIG. 2 sets forth an illustration of K channel function and the control of corporal smooth muscle tone. $K^+$ ion flux is controlled by three main effector pathways, the first two are the cAMP/PKA (PKA: protein kinase A) and cGMP/PKG (protein kinase G) pathways which are activated by $PGE_1$ and $NO^-$, respectively, and these pathways clearly modulate the activity of the maxi-K channel; their effects on the $K_{ATP}$ channel have not been documented. The third pathway is the potassium channel modulators, which modulate the activity of the $K_{ATP}$ channel. Because of the disposition of these ions in the intra- and extracellular spaces, the opening of $Ca^{2+}$ channels leads to the influx of $Ca^{2+}$ down it's electrochemical gradient and subsequent intracellular depolarization, while the opening of K channels leads to efflux of K+ from the cell down its electrochemical gradient, and subsequent intracellular hyperpolarization. The effects of these reciprocal pathways on membrane potential and the level of corporal smooth muscle tone are exerted, at least in part, through modulation of the intracellular calcium concentration, with increases in intracellular calcium associated with contraction, and decreases in intracellular calcium associated with relaxation. (+) denotes a positive or stimulatory effect; (−) denoted a negative or inhibitory effect; ? denoted an unknown action; $PIP_2$: phosphatidylinositol bisphosphate; DAG: diacylglcerol; $IP_3$: inositoltrisphosphate; $NO^-$: nitric oxide; NTG:the nitrate donor nitroglycerin; ET- 1: endothelin- 1; PE: phenylephrine; L-type $Ca^{2+}$:L-type, voltage dependent calcium channel.

FIG. 3: FIG. 3 illustrates the surgical preparation and placement of pressure monitoring cannulae. As shown, the rat is anaesthetized and lying supine. The arterial line in the left carotid artery is connected to a MacLab data acquisition board via a transducer and transducer amplifier, for continuous monitoring of blood pressure. A right external jugular venous line is utilized for intravenous fluid transfusion or blood sampling. As shown, the prostate has been exposed by a lower midline incision. The cavernous nerves are seen on the posterolateral surface of the prostate arising from the pelvic ganglion which is formed by the joining of the hypogastric and pelvic nerves. The two corpora have been exposed by inguinoscrotal incisions on both sides, combined with degloving of the penis. A line is inserted into the right corpora for continuous monitoring of intracorporal pressure via the MacLab instrumentation. Yet another line is inserted in the left corpora for intracavernous drug injection. Lastly, the nerve stimulator probe is placed around the cavernous for current stimulation.

FIG. 4.

FIG. 5: FIG. 5 sets forth a diagram indicating the major mechanisms regulating corporal smooth muscle tone. Shown are two corporal smooth muscle cells, interconnected by a gap junction plaque at their lateral border. Also shown are voltage-dependent Ca channels, and K channels. The left cell depicts the series of intracellular events linked to corporal smooth muscle contraction (an elevation in intracellular calcium levels), while the right depicts the series of intracellular events linked to corporal smooth muscle relaxation (a decrease in intracellular $Ca^{2+}$ levels). +: means a stimulatory, positive or increasing effect, and −: means a inhibitory or negative effect.

DETAILED DESCRIPTION OF THE INVENTION

The present invention provides a method of gene therapy for erectile dysfunction through delivery and expression of a recombinant vector containing a DNA sequence encoding a protein involved in the regulation of smooth muscle tone in a smooth muscle cell. The DNA sequence may be genomic DNA or cDNA.

The present invention further provides a method of gene therapy wherein the protein involved in the regulation of smooth muscle tone modulates vasorelaxation. Examples of proteins which modulate vasorelaxation include, for example, nitric oxide synthase, guanylate cyclase, adenylate cyclase, protein kinase G, protein kinase A, potassium channels, calcium channels, and any combination thereof. These proteins will enhance smooth muscle relaxation resulting in a more easily attained erection Also contemplated for use in the method of the present invention is a DNA sequence that encodes a protein that acts to inhibit a protein that modulates vasoconstriction of smooth muscle. An example of a protein that modulates vasoconstriction of corporal smooth muscle is protein kinase C. Proteins which inhibit those proteins that are involved in the vasoconstriction of the smooth muscle cell will ultimately cause enhanced corporal smooth muscle relaxation and a more easily attained erection; exerting their effects, at least in part, via decreases in intracellular $Ca^{2+}$ levels and altered myofilament sensitivity.

Examples of smooth muscle cells for which the method of gene therapy may be used include, but are not limited to, corporal smooth muscle cells and arterial smooth muscle cells. Given the many histological and physiological similarities between corporal smooth muscle cells and other vascular tissue, it follows naturally that similar principles would apply to the arterial smooth muscle cells of the penis.

The DNA sequence may be introduced into the smooth muscle cell by a number of procedures known to one skilled in the art, such as electroporation, DEAE Dextran, monocationic liposome fusion, polycationic liposome fusion, protoplast fusion, DNA coated microprojectile bombardment, by creation of an in vivo electrical field, injection with recombinant replication-defective viruses, homologous recombination, and naked DNA transfer. It is to be appreciated by one skilled in the art that any of the above methods of DNA transfer may be combined.

The present invention also provides a method of inducing penile erection in a subject comprising the introduction and expression of a DNA sequence encoding a protein involved in the regulation of smooth muscle tone into a sufficient number of smooth muscle cells of the subject to induce penile erection in the subject. In a preferred embodiment, the method of the present invention is used to alleviate erectile dysfunction. The erectile dysfunction may result from a variety of disorders including neurogenic, arteriogenic and veno-occlusive dysfunctions as well as other conditions which cause incomplete relaxation of the smooth muscle. The subject may be animal or human, and is preferably human.

The introduction of the DNA sequence into the cells of the subject may be effected by methods known to one skilled in the art, such as electroporation, DEAE Dextran, cationic liposome fusion, protoplast fusion, by creation of an in vivo electrical field, DNA coated microprojectile bombardment, injection with recombinant replication-defective viruses, homologous recombination, and naked DNA transfer. It will be appreciated by those skilled in the art that any of the above methods of DNA transfer may be combined. In a preferred embodiment of the invention, DNA transfer is the preferred method.

For the purposes of naked DNA transfer into smooth muscle cells, the recombinant vector of the present invention, which contains the gene for expression, may be combined with a sterile aqueous solution which is preferably isotonic with the blood of the recipient. Such formulations may be prepared by suspending the recombinant vector in water containing physiologically compatible substances such as sodium chloride, glycine, and the like, and having buffered pH compatible with physiological conditions to produce an aqueous solution, and rendering such solution sterile. In a preferred embodiment of the invention, the recombinant vector is combined with a 20–25% sucrose in saline solution in preparation for introduction into a smooth muscle cell.

The recombinant vector of the present invention containing the DNA sequence for expression may also be incorporated into cationic liposomes and directly injected into the smooth muscle cells of the subject. In a preferred embodiment of the invention, the transfer of the DNA sequence encoding a protein involved in the regulation of smooth muscle tone is by naked DNA transfer.

The present invention also provides a recombinant vector comprising (1) the nucleic acid of or corresponding to at least a portion of the genome of a virus, which portion is capable of directing the expression of a DNA sequence, and (2) a DNA sequence encoding a protein involved in the regulation of smooth muscle tone operably linked to the viral nucleic acid and capable of being expressed as a functional gene product in the target cell. The recombinant viral vectors of the present invention may be derived from a variety of viral nucleic acids known to one skilled in the art, e.g. the genomes of HSV, adenovirus, adeno-associated virus, Semiliki Forest virus, vaccinia virus, and other viruses, including RNA and DNA viruses.

The recombinant vectors of the present invention also contain a nucleotide sequence encoding suitable regulatory elements so as to effect expression of the vector construct in a suitable host cell. As used herein, "expression" refers to the ability of the vector to transcribe the inserted DNA sequence into mRNA so that synthesis of the protein encoded by the inserted nucleic acid can occur. Those skilled in the art will appreciate that a variety of enhancers and promoters are suitable for use in the constructs of the invention, and that the constructs will contain the necessary start, termination, and control sequences for proper transcription and processing of the DNA sequence encoding a protein involved in the regulation of smooth muscle tone when the recombinant vector construct is introduced into a host cell.

Vectors suitable for the expression of the DNA sequence encoding a protein involved in the regulation of smooth muscle tone in a smooth muscle cell are well known to one skilled in the art and include pET-3d (Novagen), pProEx-1 (Life Technologies), pFastBac 1 (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSET A,B,C (Invitrogen), pYES2 (Invitrogen), pAC360 (Invitrogen), pVL1392 and pV11392 (Invitrogen), pCDM8 (Invitrogen), pcDNA I (Invitrogen), pcDNA I(amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors would be apparent to one skilled in the art.

Suitable promoters include, but are not limited to, constitutive promoters, tissue specific promoters, and inducible promoters. In one embodiment of the invention, expression of the DNA sequence encoding a protein involved in the regulation of smooth muscle tone is controlled and affected by the particular vector into which the DNA sequence has been introduced. Some eukaryotic vectors have been engineered so that they are capable of expressing inserted nucleic acids to high levels within the host cell. Such vectors utilize one of a number of powerful promoters to direct the high level of expression. Eukaryotic vectors use promoter-enhancer sequences of viral genes, especially those of tumor viruses. This particular embodiment of the invention provides for regulation of expression of the DNA sequence encoding the protein using inducible promoters. Non-limiting examples of inducible promoters include, but are not limited to, metallothionine promoters and mouse mammary tumor virus promoters. Depending on the vector, expression of the DNA sequence in the smooth muscle cell would be induced by the addition of a specific compound at a certain point in the growth cycle of the cell. Other examples of promoters and enhancers effective for use in the recombinant vectors of the present invention include, but are not limited to, CMV (cytomegalovirus), SV40 (simian virus 40), HSV (herpes simplex virus), EBV (epstein-barr virus), retroviral, adenoviral promoters and enhancers, and smooth muscle specific promoters and enhancers.

The present invention further provides a smooth muscle cell which expresses a DNA sequence encoding a protein involved in the regulation of smooth muscle tone. As used herein, "exogenous" means the DNA sequence is introduced from outside the organism. The introduction of the recombinant vector containing the DNA sequence into the smooth muscle cell may be effected by methods known to one skilled in the art, such as electroporation, DEAE Dextran, cationic liposome fusion, protoplast fusion, DNA coated microprojectile bombardment, injection with recombinant replication-defective viruses, homologous recombination, and naked DNA transfer. It will be appreciated by those skilled in the art that any of the above methods of DNA transfer may be combined.

Figure 5:
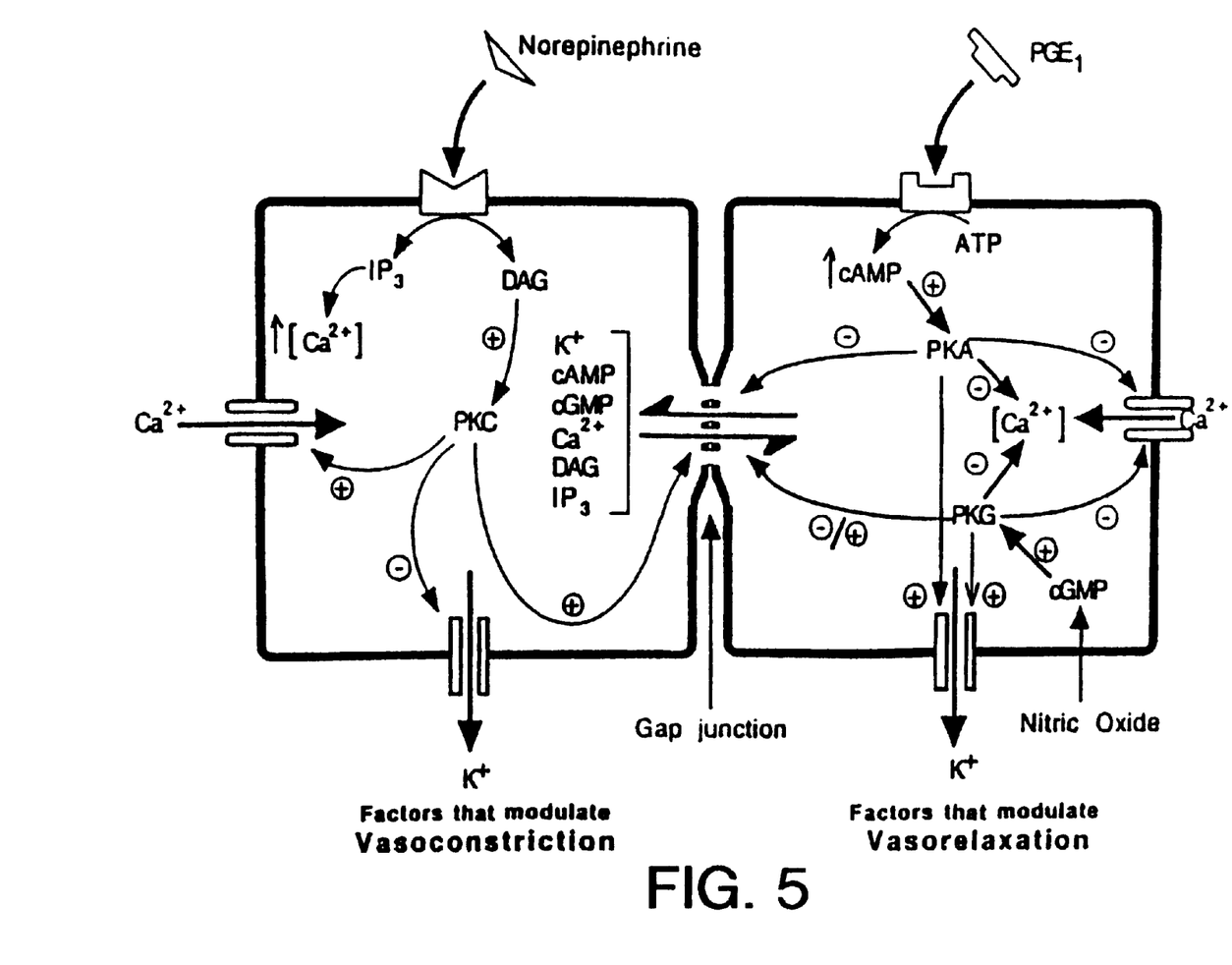

Of critical importance with respect to all in vivo gene therapy approaches is the percentage of target cells that must be affected, and the relative efficiency of affecting only the desired cell type(s) to see a physiologically relevant therapeutic effect. In this regard, there are two main reasons for suspecting that gene therapy of erectile dysfunction may be inherently more successful than its proposed uses in other, more systemic, cardiovascular disorders, such as those outlined above:

It is a well documented fact that corporal and arterial smooth muscle cells are interconnected by a ubiquitously distributed population of intercellular channels known as gap junction proteins both in vivo and in vitro (Christ, G. J., et al. *Life Sciences* 49.24 (1991) PL195–200; Christ, G. J., et al. *International Journal of Impotence Research* 5.2 (1993) 77–96; Christ, G. J., et al. *Journal of Pharmacology & Experimental Therapeutics* 266.2 (1993) 1054–65; Christ, G. J., et al. *Biophysical Journal* 67.3 (1994) 1335–44;

Christ, G. J., *Urological Clinic of North America*, 22.4 (1995) 727–745; Christ, G. J. *World Journal of Urology* (1997) (in press); Christ, et al., *Circulation Research*, 79 (1996) 631–646; Christ & Melman, *Molecular Urology* (1997) (in press)), the mechanisms for which are depicted in FIG. 5.

Figure 2:
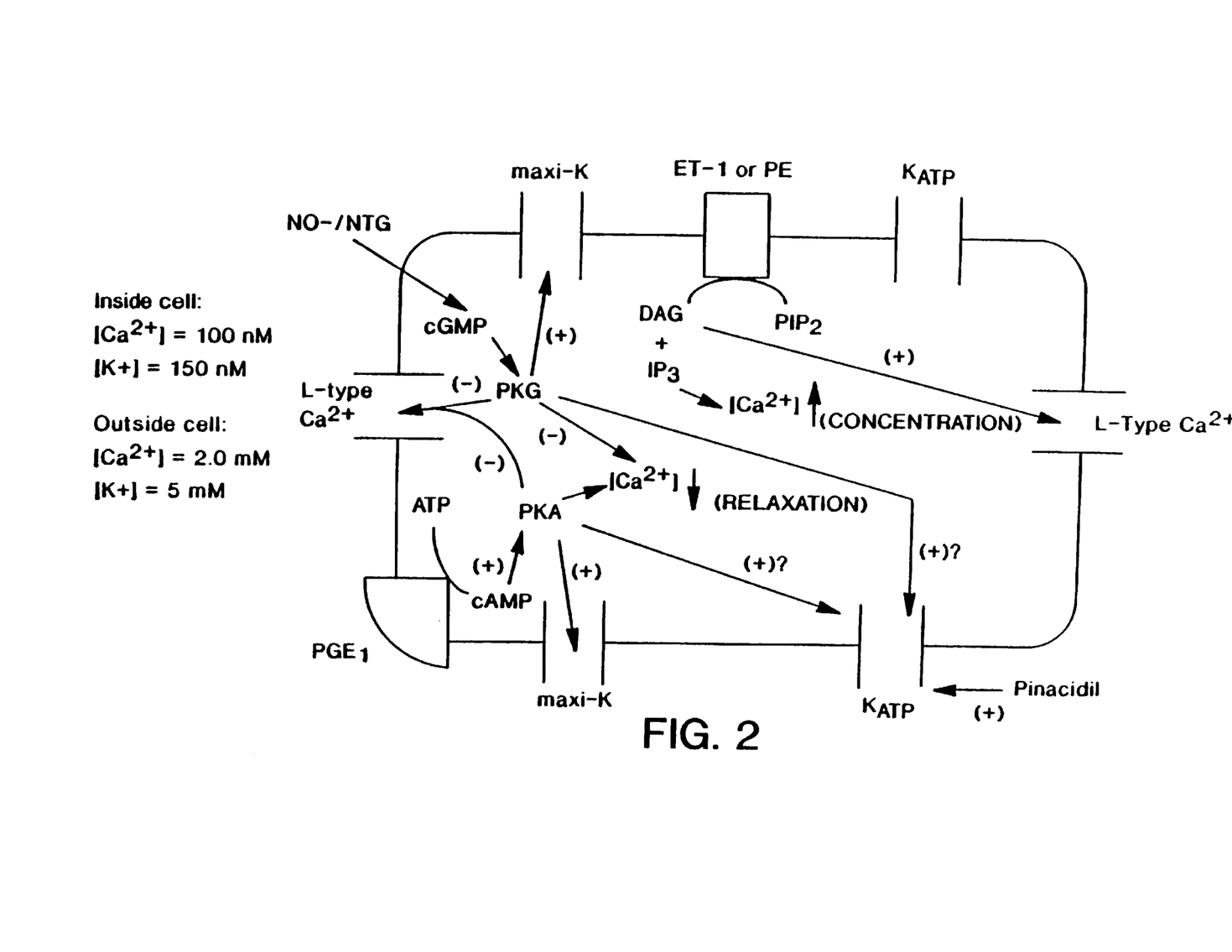

In the corpora, smooth muscle contraction (i.e. elevation in intracellular calcium levels) might be accomplished following activation of the $\alpha_1$-adrenergic receptor by norepinephrine, or by endothelin-1 activation of the $ET_A$ receptor. In both cases, receptor activation leads to $Ca^{2+}$ mobilization. Specifically, activation of these receptors by norepinephrine or ET-1 leads to activation of phospholipase C, which cleaves membrane bound phosphatidyl inositol ($PIP_2$) into $IP_3$ and diacylglycerol (DAG). As illustrated in FIG. 2, increases in DAG and IP3 ultimately exert their effects, at least in part, via increase in intracellular $Ca^{2+}$ levels. Conversely, any physiological event resulting in a diminution of transmembrane $Ca^{2+}$ flux, or sequestration of intracellular $Ca^{2+}$, e.g. membrane hyperpolarization, will result in smooth muscle relaxation. As such, $PGE_1$ activates the $PGE_1$ receptor, to stimulate the adenylate cyclase enzyme, which then catalyzes the conversion of ATP to cAMP. Increased cAMP then stimulates protein kinase A (PKA). Alternately, smooth muscle relaxation can be achieved by nitric oxide, released from endothelial or neuronal sources. Nitric oxide diffuses into smooth muscle cells to activate soluble guanylate cyclase, that catalyzes the conversion of GTP to cGMP. Elevated cGMP levels activate protein kinase G (PKG). The effects of PKA, PKG, and PKC on gap junctions, K channels, and $Ca^{2+}$ channels are thought to be mediated via phosphorylation of specific amino acid residues on target proteins (gap junctions, K channels, and $Ca^{2+}$ channels). FIG. 5 illustrates the result of their putative actions as follows: +: means a stimulatory, positive or increasing effect, and –: means a inhibitory or negative effect. This simplified model illustrates how the interactions of these important second messenger systems might impact on gap junctions, K, and $Ca^{2+}$ channels, and thus modulate corporal smooth muscle tone in vitro and in vivo.

Connexin43 is the predominant isoform expressed in the human penis. These intercellular channels provide partial cytoplasmic continuity between adjacent smooth muscle cells, allowing the intercellular exchange of physiologically relevant ions (K+ and $Ca^{2+}$) and second messenger molecules ($IP_3$, cAMP, cGMP). This is an extremely important point given the relatively sparse autonomic innervation of the corporal parenchyma, even in the healthy male. Thus, the presence of gap junctions provides the anatomic substrate required for the rapid and syncytial contraction and relaxation responses required of the corporal smooth muscle cells for normal penile erection, as well as detumescence. In this fashion, even in the healthy male, the presence of gap junctions allows smooth muscle cells not directly activated by a relevant neuronal signal to be rapidly, albeit indirectly, recruited into the contraction or relaxation response by this prominent intercellular pathway. The experimental and clinical evidence verifying the validity of this supposition has been outlined in recent publications (Christ, G. J., et al., *Circulation Research*, 79:631–646 (1996); Christ, G. J., *World Journal of Urology*, (1997) (in press)), and a mathematical model has been constructed that accounts for this behavior (Christ, G. J., et al., *Journal of Urology* 155:620A (Abstract) (1996); Christ, G. J., et al., *FASEB J.* 9: A914 (1995)). The major implication is that the presence of these gap junction channels makes it likely that only a small fraction of the corporal smooth muscle cells would need to be genetically modified to affect rather global changes in corporal smooth muscle tone.

The second major feature of the human penis that makes gene therapy an attractive possibility, is that the presence of pharmacologically induced erections in many impotent men indicates that the veno-occlusive mechanism is properly functioning in many these patients. In such patients, an erection could be pharmacologically induced by conventional intracavernous agents, while simultaneously injecting the gene(s) of interest. As such, the injected gene(s) would be expected to be largely restricted to the corporal parenchyma, because the venous outflow during a normal erection is very small (Carrier, et al. *J. Urol.* 42.4 (1993) 468–81; Andersson, et al. *Physiological Reviews* 75.1 (1995) 191–236; Lerner, et al. *J. Urol.* 149.5 Pt 2 (1993) 1246–55; Lue, et al. *J. Urol.* 137 (1987) 829). In this scenario, there would be little risk of systemic vascular side effects.

The method of gene therapy of the present invention was designed to take advantage of the fact that relatively subtle alterations in the balance between contracting and relaxing stimuli can result in profound alterations in erectile physiology and function (Lerner, et al. *J. Urol.* 149.5 Pt 2 (1993) 1246–55; Azadzoi, et al. *J. Urol.* 148.5 (1992) 1587–91; Christ, et al. *British Journal of Pharmacology* 101.2 (1990) 375–81; Christ, G. J., *Urological Clinics of North America* 22.4 (1995) 727–745; Taub, et al. *J. Urol.* 42 (1993) 698). The goal of gene therapy is to restore a more normal balance between contracting and relaxing stimuli following expression of exogenous genes that code for physiologically relevant proteins in corporal smooth muscle. If expression of these exogenous genes can be maintained for a period of weeks to months (as indicated herein the rat model), it would then permit the patient to obtain "normal" erections in the absence of any other exogenous manipulation, during this time period. Clearly this would be a major advance over all currently available therapies.

The discussion that follows outlines two specific strategies for gene therapy of erectile dysfunction. In the first case, the "sensitivity" of the smooth muscle cells will be nominally enhanced to the endogenous neuronal stimulus by transfecting the cells with the human maxi-K cDNA. In the second case, the neuronal "driving force" for erection is increased by transfecting corporal smooth muscle cells with a constitutively expressed nitric oxide synthase cDNA, bNOS. Clearly this strategy for gene therapy is explicitly dependent on both the efficacy and stability of the proposed transfection. Evidence for both is presented below.

The present invention is described in the following Experimental Details Sections which is set forth to aid in the understanding of the invention, and should not be construed to limit in any way the invention as defined in the claims which follow thereafter.

EXPERIMENTAL DETAILS SECTION

A. Materials and Methods

1. Plasmids and Genes

The pCMVβ and pcDNA3 plasmids were purchased from Invitrogen (San Diego, Calif.). The human maxi K cDNA (hslo) was obtained from Dr. Salkoff (Washington University School of Medicine, St. Louis, Mo.)(McCobb, D. P., et al. *American Journal of Physiology* 269 (1995) H767–H777). The neuronal NOS cDNA was obtained from Dr. S. Snyder (Johns Hopkins University) and Dr. D. Bredt (Univ. Calif. San Francisco)(Bredt, et al., Nature 351 (1991) 714–8). Both the human Maxi K channel cDNA (approximately 3.9 kb)(McCobb, et al. American Journal of Physiology) 269 (1995) H767–H777) and neuronal NOS cDNA (Bredt/Snyder 91287795) (Bredt, et al. Nature 351 (1991) 714–8) were inserted into the XhoI-XbaI cloning sites of the pcDNA3 vector, where expression is driven off of the CMV promoter (Invitrogen). One hundred micrograms of plasmid DNA was suspended in 200 µl sterile PBS containing 20% sucrose and injected into CC of anesthetized rats.

2. Gene Transfer of Lac Z into the Corpus Cavernosa Using Various Techniques.

Naked DNA. One hundred µg of pCMVβ plasmid (Clonetech, CA) (contains the LacZ gene under the control of the CMV promoter) in 200 µl phosphate buffered saline (containing 20% sucrose) were injected into corpus cavernosum into 3 month old Fischer rats (under anesthesia). Ten days later CC tissue was resected and stained for β-galactosidase activity.

Liposomes. Five micrograms of pCMVβ plasmid in 100 µl PBS were mixed with 100 µl Lipofectin reagent (Gibco), and the resultant liposome complexes (200 µl) were injected into corpus cavernosum into 3 month old Fischer rats (under anesthesia). Ten days later CC tissue was resected and stained for β-galactosidase activity.

Adenovirus Vector. Two hundred microliters of Adenovirus vectors (>$10^{10}$ pfu/ml) containing the lacZ cDNA were obtained from Dr. Roy Chowdhury (AECOM gene therapy core) and injected intra CC in 3 month old Fischer rats (under anesthesia). Three days later CC tissue was resected and stained for β-galactosidase activity.

3. Staining for β-galactosidase Activity

CC tissue was excised from rats at various times after injection, fixed with 4% paraformaldehyde/0.1% glutaraldehyde for 3 hours, and stained with X-Gal for 15 hrs. at 37° C. (Vitadello, M., et al. Human Gene Therapy 5 (1994) 11–8).

Animal. 62 male Sprague Dwaley (Taconic Farms, Germantown, N.Y.) 10–20 weeks old, and weighing 200–250 g were used in these experiments. All rats were fed Purina lab rodent chow ad libitum and housed individually with 07.00–19.00 light cycle. Rats were divided into the groups indicated Table 1.

TABLE 1

Gene Transfer and Time Course Experiments

| Group | Rats | Age | Gene Therapy | Method of Gene Transfer | Time Course Experiments |
|---|---|---|---|---|---|
| A | n = 12 | 10 week | Lac Z (n = 9) | Adenovirus (n = 3) Liposome (n = 3) Naked DNA (n = 3) | |
| | | | Control (n = 3) | | |
| B | n = 24 | 10 week | Lac Z (n = 12) | Naked DNA | 2 week (n = 3) 4 week (n = 3) 8 week (n = 3) 12 week (n = 3) |
| | | | Control (n = 12) | (Sham) | 2 week (n = 3) 4 week (n = 3) 8 week (n = 3) 12 week (n = 3) |
| C | n = 20 | 20 week | NOS (n = 12) | Naked DNA | 1 month (n = 2) 2 month (n = 4) 3 month (n = 4) 4 month (n = 2) |

TABLE 1-continued

Gene Transfer and Time Course Experiments

| Group | Rats | Age | Gene Therapy | Method of Gene Transfer | Time Course Experiments |
|---|---|---|---|---|---|
| | | | Control (n = 8) | (Sham control) | 1 month (n = 2) 2 month (n = 2) 3 month (n = 2) 4 month (n = 2) |
| D | n = 18 | 20 week | Maxi K (n = 10) | Naked DNA | 1 month (n = 2) 2 month (n = 4) 3 month (n = 2) 4 month (n = 2) |
| | | | Control (n = 8) | (Sham control) | 1 month (n = 2) 2 month (n = 2) 3 month (n = 2) 4 month (n = 2) |

4. Preparation of Animals for In vivo Erectile Studies

Induction of anesthesia. The rats were anaesthetized by intraperitoneal injection (35 mg/kg) of sodium pentobarbital (Anpro Pharmaceuticals). Anesthesia was maintained during the course of the experimental protocol (2–3 hrs) by subsequent injection of pentobarbital (5–10 mg/kg) every 45–60 minutes, as required for maintenance of anesthesia.

Figure 3:
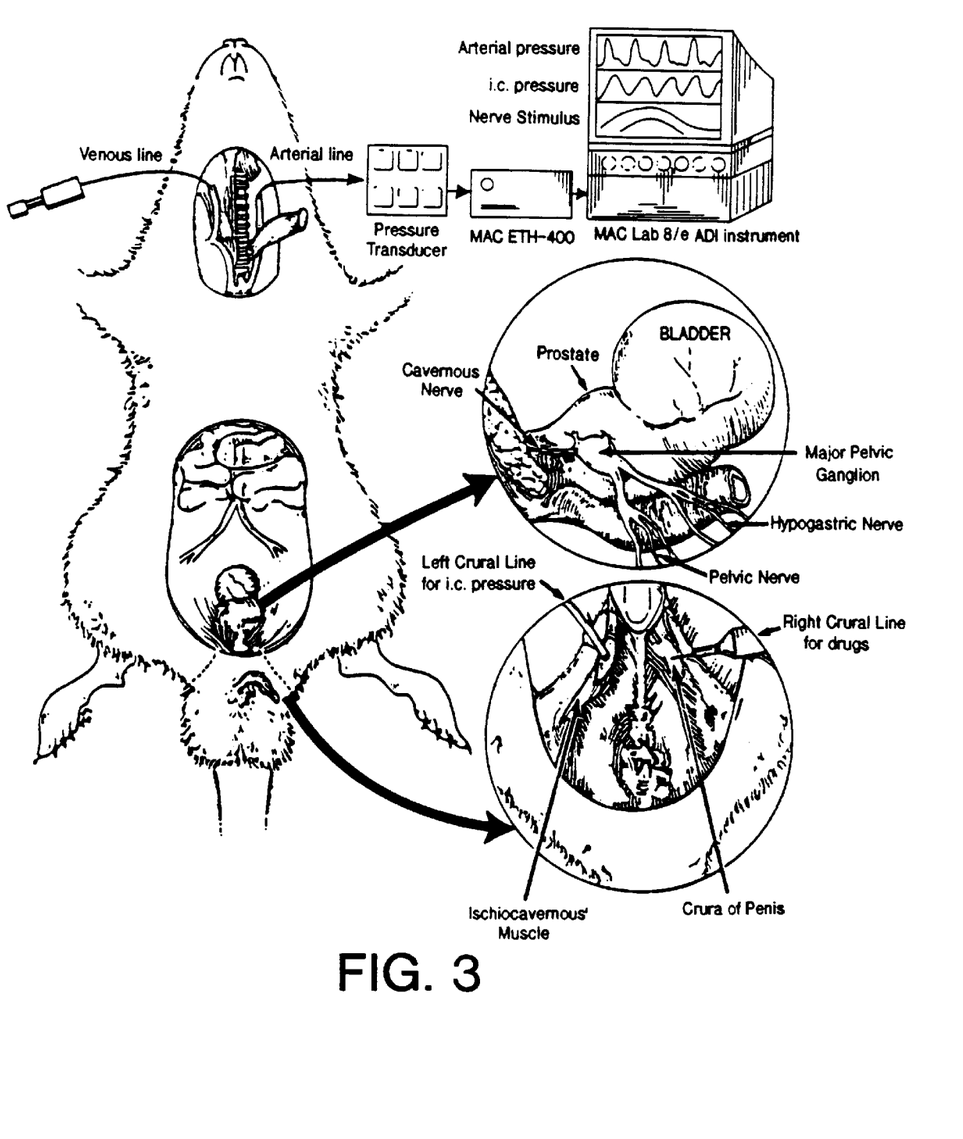

Surgical preparation and placement of pressure monitoring cannulae. FIG. 3 illustrates the entire experimental procedure. Animals were placed in the supine position and the bladder and prostate were exposed through a midline abdominal incision. The inferior hypogastric plexus (i.e., the pelvic plexus or major pelvic ganglia), pelvic nerves and the cavernous nerve were identified posterolateral to the prostate on both sides, and the stainless-steel bipolar wire electrodes were placed around these structures for electrical stimulation. The penis was denuded of skin, both crura were exposed by removing part of the overlying ischiocavernous muscle. In order to monitor intracavernous pressure (ICP), a 23-gauge cannula was filled with 250 U/ml of heparin solution, connected to PE-50 tubing (Intramedic, Becton Dickinson;) and inserted into the right corpus cavernosum. The tubing was then fixed to the tunica with a 7-0 Dermalon suture, to ensure stability during measurement of ICP. Another 23 gauge cannula was connected to a 1 ml syringe and inserted into left corpus cavernosum for intracavernous drug injection. Systemic arterial blood pressure (BP) was monitored via a 25-gauge cannula placed into the carotid artery.

Both pressure lines (BP) and (ICP) were connected to a pressure transducer, which was, in turn, connected via a Transducer amplifier (ETH 400 CB Sciences, Inc) to a data acquisition board (Mac Lab/8e7, ADI Instruments, MA). Real-time display and recording of pressure measurements was performed on a Macintosh computer (Mac Lab software V3.4). The pressure transducers and AID board were calibrated in cm of $H_2O$.

Neurostimulation of cavernous nerve and recording of intracavernosal pressure. Direct electrostimulation of the cavernous nerve was performed with a delicate stainless-steel bipolar hook electrode attached to the multijointed clamp. Each probe was 0.2 mm in diameter; the two poles were separated by 1 mm. Monophasic rectangular pulses were delivered by a signal generator (custom made and with built in constant current amplifier). Stimulation parameters were as follows: frequency; 20 Hz, pulse width; 0.22 msec, duration; 1 minute. The current protocol was the application of increasing current at the following intervals: 0.5, 1, 2, 4, 6, 8 and 10 mA. The changes in intracavernous pressure and systemic blood pressure were recorded at each level of neurostimulation.

5. Tissue Procurement and Fixation and Immunohistochemistry Analysis

Tissue retrieval. Following completion of the neurostimulation experiments the penises of both the gene therapy and age-matched control animals were harvested, and the distal end of the penis marked with methylene blue to ensure the proper later identification of the distal and proximal ends. All penile tissue was immediately transferred to 4% paraformaldehyde in phosphate buffer pH 7.4 for fixation for 4 hours at 20° C., and later cryoprotected in cold 30% sucrose in 0.1 M phosphate buffer (PBS; at 4° C. overnight or longer), pH 7.4 for immunostaining. Part of the penis of the animal was frozen in liquid nitrogen and preserved at 80° C. for molecular biological studies. Briefly, the tissue was sectioned on a cryostat at 14 μm and the sections were dried onto slides and paraffin embedded. The slides were stored at −20° C. until they were stained which was usually within 2–4 weeks.

Histology. Histological examination of the sections were performed to confirm the identification of nerves and smooth muscles. Serial, slide-mounted sections were fixed in 10% formalin and stained with hematoxylin and eosin. All slide preparation specimens were viewed with Zeiss microscope.

Nitric Oxide Synthase Immunohistochemistry. Slide mounted tissue sections were deparaffinized with xylene, rehydrated in graded alcohols and blocked for endogenous peroxidase activity with 3% hydrogen peroxide. Nonspecific binding of antibodies to the specimens was blocked by incubation with 1.5% normal goat serum in phosphate-buffered saline (PBS) for 30 minutes at room temperature. The slides were then drained and incubated for one hour at room temperature with primary antibody. The antibody used was a rabbit polyclonal antibody directed against brain NOS (Transduction Laboratories, Lexington Ky.). An antibody concentration of 1.0 μg/ml was found to be optimal for immunostaining. Antigen binding was detected by the avidin-biotin immunoperoxidase method, using the VectaStain Elite ABC kit. The color reaction was developed with diaminobenzidine activated with hydrogen peroxide (diaminobenzidine as the chromogen) and then counterstained with hematoxylin solution. Staining was not evident in the negative control which substituted PBS for primary antibody, supporting the specificity of primary antibody used in our experiment.

Statistical analysis. All statistical analyses were performed using the Stat-View 4.5 software (Abacus Concepts, Berkeley, Calif.). A two-tailed Student t test for unrelated samples was utilized for comparison of group means for parameters of interest between gene therapy rats (NOS or Maxi-K) and age-matched control animals. All differences were considered significant at p <0.05. Unless otherwise stated, all data are expressed as the mean S.E.M.

Analysis of Neurostimulation Data. Stimulus response curves were generated for neurostimulation by plotting the fractional change in corporal pressure as a function of mean systemic blood pressure (expressed as ICP/BP) for stepwise increases in current (1,2,4,6,8,10 mA)(Sigma Plot Mac V5.0 Jandel Scientific, San Rafael, Calif.) both for control and gene therapy rats.

6. Gene Transfer of Lac Z into Smooth Muscle Cells of the Rat Corpus Cavernosum.

Gene transfer into vascular smooth muscle cells has been achieved using various techniques, such as retroviruses, adenoviruses, cationic liposomes, or naked DNA transfer. To determine the efficiency of these techniques for in vivo, intracorpus cavernosal gene transfer, the plasmid pCMβ was injected as naked DNA or incorporated into cationic liposomes, or recombinant adenovirus containing the Lac Z cDNA (coding for β-galactosidase), each into CC tissue of three rats. All three techniques of gene transfer produced positive results, but adenoviral mediated gene transfer was the most effective, as evidenced, on the whole tissue level, by the conversion of the chromogenic substrate, X-Gal (5-bromo-4-chloro-3-indolyl-b-D-galactoside) into its blue breakdown product by the activity of β-galactosidase.

To determine the relative number and histologic type of cells expressing β-galactosidase, one hundred μg of pCMVβ plasmid in 200 μl phosphate buffered saline (containing 20% sucrose) were injected into the CC of 3 month old Fischer rats (under anesthesia). Thirty days later, CC from injected and control rats were excised, fixed with 4% paraformaldehyde/0.1% glutaraldehyde for 3 hours, and reacted with X-Gal for 15 hrs. at 37° C., paraffin embedded and sectioned (Vitadello, M., et al. *Human Gene Therapy* 5 (1994) 11–8). As depicted in FIG. 2, β-galactosidase activity is evident in a significant number of the smooth muscle cells thirty days after DNA injection.

7. Increased Intracorporal Pressure Following Injection of cDNA for Neuronal NOS or Potassium Channel Maxi-K The human Maxi-K channel cDNA (hSlo) (approximately 3900 nucleotides) (McCobb) and neuronal NOS cDNA (approximately 5000 nucleotides) (Bredt/Snyder 91287795) were inserted into the XhoI-XbaI cloning sites of the pcDNA3 vector, where expression is driven off of the Cytomegalovirus promoter. One hundred μg of each plasmid, in 200 μl phosphate buffered saline, (containing 20% sucrose) was injected into the CC of 4 month old Fischer rats (under anesthesia). Control rats were either sham operated, sham operated with an intracorporal injection of 200 μl PBS containing 20% sucrose, or sham operated with an intracorporal injection of 200 μl PBS containing 20% sucrose and 100 μg pCDNA vector DNA. Basal and nerve-stimulated intracorporal pressures (ICP) were measured between 2 weeks and 4 months after injection. No significant differences were observed in intracorporal pressures within the time frame examined, and results from all animals within each group were pooled. Likewise, no significant differences were observed among the various controls, and all control data was pooled.

Figure 4:
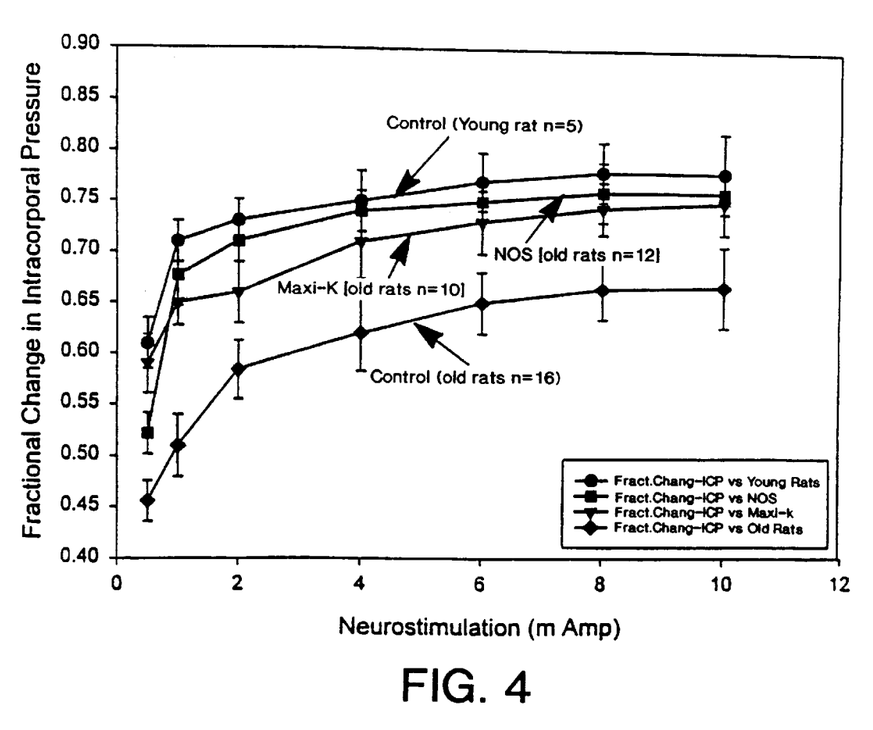
FIG. 4 sets forth the results of experiments determining the fractional change in intracavernous pressure (ICP) in response to neurostimulation.

The data depicted in FIG. 4 and Tables 2 and 3 below indicate that the injection of either the NOS or Maxi-K cDNAs significantly increased both basal and nerve-stimulated ICP. Mean basal fractional change in ICP increased from a control level of ≈8 (cm of $H_2O$) to ≈14 in NOS-injected rats, to ≈13 in Maxi K-injected rats. In a similar manner, the nerve-stimulated fractional change in ICP was approximately 30% higher in both NOS and maxi K-injected rats, over a range of 2–10 milli amp stimulation.

TABLE 2

Intracavernous pressure (ICP) response following nerve stimulation in NOS and control group

| | | | | Cavernous Nerve Stimulation* | | | | |
|---|---|---|---|---|---|---|---|---|
| | ICP♣ (Basal) | ICP◆ 0.5 mA♥ M ± SEM♠ | ICP 1 mA M ± SEM | ICP 2 mA M ± SEM | ICP 4 mA M ± SEM | ICP 6 mA M ± SEM | ICP 8 mA M ± SEM | ICP 10 mA M ± SEM |
| NOS gene therapy (n = 12) | 14.62 ± .64 | 60.02 ± 5.9 | 102.50 ± 3.89 | 110.49 ± 4.65 | 113.93 ± 2.17 | 117.72 ± 2.80 | 121.26 ± 3.26 | 129.03 ± 5.4 |
| Sham rats received vehicle only (n = 8) | 8.1 ± .37 | 45.81 ± 3.63 | 75.242 ± 3.59 | 83.93 ± 3.23 | 83.59 ± 4.52 | 85.67 ± 3.75 | 87.94 ± 4.45 | 92.23 ± 3.62 |
| P value | .0001 | .0085 | .0001 | .0001 | .0001 | .0001 | .0001 | .0003 |

*Cavernous nerve stimulation performed on both sides (Observation × 2 the # of rats)
◆ICP-Intracorporal pressure in cm of $H_2O$
♣BCP-Basal corporal pressure in cm of $H_2O$ before neurostimulation
♥mA-milli Amperes of stimulus to the nerve
♠M ± SEM-Mean and standard error of the mean

TABLE 3

Intracavernous pressure (ICP) response following nerve stimulation in maxi-K and control group

| | | | | Cavernous Nerve Stimulation* | | | | |
|---|---|---|---|---|---|---|---|---|
| | ICP♣ (Basal) | ICP◆ 0.5 mA♥ M ± SEM♠ | ICP 1 mA M ± SEM | ICP 2 mA M ± SEM | ICP 4 mA M ± SEM | ICP 6 mA M ± SEM | ICP 8 mA M ± SEM | ICP 10 mA M ± SEM |
| maxi-K gene therapy (n = 10) | 13.13 ± .60 | 65.21 ± 3.35 | 99.81 ± 3.19 | 103.21 ± 3.05 | 108.12 ± 3.97 | 112.67 ± 3.50 | 115.45 ± 7.99 | 129.50 ± 4.83 |
| Sham rats received vehicle only (n = 8) | 8.16 ± .37 | 45.81 ± 3.63 | 75.24 ± 3.59 | 80.99 ± 3.25 | 83.97 ± 3.23 | 85.67 ± 3.75 | 87.94 ± 4.45 | 92.23 ± 3.62 |
| P value | .0001 | .0030 | .0001 | .0002 | .0001 | .002 | .0003 | .0002 |

*Cavernous nerve stimulation performed on both sides (Observation × 2 the # of rats)
◆ICP-Intracorporal pressure in cm of $H_2O$
♣BCP-Basal corporal pressure in cm of $H_2O$ before neurostimulation
♥mA-milli Amperes of stimulus to the nerve
♠M ± SEM-Mean and standard error of the mean

B. Results

Potassium Channels and Corporal Smooth Muscle Function: Evidence that Altering K Channel Function Can Increase "Sensitivity" to Relaxation.

Recent studies by the inventors have indicated that hyperpolarization of corporal smooth muscle cells via activation of potassium channels represents an important mechanism for controlling corporal smooth muscle tone (Holmquist, F., et al., *J. Urol.* 144 (1990) 146; Christ, G. J., et al., *Journal of Andrology* 14.5 (1993) 319–28; Fan, S. F., et al., *J. Urol.* 153 (1995) 818; Christ, G. J., *Urological Clinics of North America* 22.4 (1995) 727–745). This observation reflects the fact that sustained contraction of human corporal smooth muscle, which is characteristic of flaccidity (the condition the vast majority of the time) is largely dependent on continuous transmembrane $Ca^{2+}$ flux through voltage-gated $Ca^{2+}$ channels. The activity of these voltage dependent calcium channels in corporal smooth muscle cells is, in turn, closely modulated by hyperpolarizing currents, initiated and carried mainly by K channels. Among the subtypes of K+ channels, the ≈180 pS $Ca^{2+}$ sensitive maxi-K channel is one of the most prominent in corporal smooth muscle cells (Fan, S. F., et al., *J. Urol.* 153 (1995) 818). Membrane hyperpolarization of corporal smooth muscle cells following activation of K channels can be accomplished by both receptor (e.g., PGE or $NO^-$)-and nonreceptor-mediated (e.g., $NO^-$ or cGMP) stimuli, derived from neuronal as well as endothelial sources. These data are summarized in FIG. 2 and Table 5.

The putative mechanism of action is thought to be as follows: release of an endogenous corporal vasorelaxant(s), for example, nitric oxide, is thought to either directly activate the K channel, or, to regulate K channel activity secondary to activation of soluble guanylate cyclase, increases in intracellular cGMP levels, activation of G kinase, and phosphorylation of cellular proteins, including nonjunctional ion channels such as K and $Ca^{2+}$ channels. Increased kinase activity (either A or G) has opposing action on $Ca^{2+}$ and K channels, resulting in decreased activity of the former and increased activity of the latter. Thus, an elevation in intracellular $NO^-$ and/or cGMP levels can result in both activation of K channels and inhibition of $Ca^{2+}$ channels. The algebraic sum of these two opposing effects is to significantly diminish transmembrane calcium flux, resulting in diminished corporal smooth muscle tone, and thus, corporal smooth muscle relaxation.

Since the activity of the maxi-K channel appears to be modulated by all of the physiologically relevant endogenous regulators of corporal smooth muscle tone (FIG. 2), including PGE (Zhang, et al., *Journal of Urology*, 155:678A (1996); Zhao, et al., *J. Urol.* 154 (1995) 1571–1579; Zhao, et al., *Journal of Urology*, 155:678A (1996) as well as NO$^-$ (Christ, et al., unpublished observations), it is clearly an important final common mediator of the degree of corporal smooth muscle tone. Consistent with this hypothesis, the inventors have preliminary evidence that altered regulation/function of this channel may represent an important feature of the presence of organic erectile dysfunction per se, in human corporal smooth muscle (Fan, S. F., et al., *J. Urol.* 153 (1995) 818; Christ, G. J., *Urologic Clinics of North America*, 22.4:727–745 (1995); Christ, G. J., et al., *Journal of Urology*, 155:620A (1996)). For all of these reasons, the inventors feel that the relatively stable transfection of corporal smooth muscle cells with the human smooth muscle maxi-K channel cDNA represents an important and attractive strategy for modulating erectile capacity.

Nitric Oxide and Corporal Smooth Muscle Function: Evidence that Increasing the Amount of NO$^-$ Expressed in Corporal Tissue Can Increase the "Driving Force" for Relaxation.

An abundance of recent experimental evidence documents the important role played by nitric oxide (NO$^-$) in arterial and corporal smooth muscle relaxation, and thus, penile erection (Argiolas, et al., *Neuropharmacology* 33.11 (1994) 1339–44; Burnett, et al., *Science* 257.5068 (1992) 401–3; Trigo-Rocha, et al., *J. of Physiology* 264.2 Pt 2 (1993) H419–22; Burnett, et al. *Biology of Reproduction* 52.3 (1995) 485–9). For example, electrical stimulation of both human (Saenz de Tejada, et al., *New England Journal of Medicine* 320.16 (1989) 1025–30) and rabbit (Ignarro, et al., *Biochem Biophys Res Commun* 170 (1990) 843–850) corpus cavernosal muscle strips results in smooth muscle relaxation. These responses are thought to be mediated via release of nitric oxide. Consistent with this supposition, these relaxation responses can inhibited by nitroglycerin-substituted analogs of L-arginine, which block NO$^-$ formation (Ignarro, et al., *Biochem Biophys Res Commun* 170 (1990) 843–850; Holmquist, et al., *Acta Physiol Scand* 141 (1991) 441–442; Kim, et al., *J. Clin. Invest.* 88 (1991) 112–118). Further, the relaxation of both rabbit and human corporeal smooth muscle can be induced through compounds that release NO$^-$ (Ignarro, et al., *Biochem Biophys Res Commun* 170 (1990) 843–850; Rajfer, et al., *New England Journal of Medicine* 326 (1992) 90–94; Christ, G. J., et al. *Urological Clinics of North America* 22.4 (1995) 727–745). Moreover, the importance of the NO$^-$ dependent pathway for relaxation of human corporal smooth muscle has also been documented (Bush, et al., *J. Urol.* 147 (1992) 1650–1655; Trigo-Rocha, et al., *Neurology & Urodynamics* 13.1 (1994) 71–80; Christ, et al., *Canadian Journal of Physiology and Pharmacology*, 73:714–726 (1995)).

Nitric oxide is produced by the enzyme nitric oxide synthase (NOS) as a product of the enzymatic conversion of L-arginine to L-citrulline. NO$^-$ is produced in endothelial cells upon cholinergic stimulation or by neuronal sources (released from NANC nerve terminals). With respect to the latter, NO$^-$ is a novel neurotransmitter in that it is not stored in synaptic vesicles in nerve terminals but is synthesized on demand. Biochemical and histochemical evidence in rabbit and rat penis suggests that the NOS isozyme which functions in penile erection belongs to the cNOS type (Burnett, et al., *Science* 257.5068 (1992) 401–3). A neural source for NOS in the rat penis was demonstrated by Keast (Keast, J. R., *Neurosciences Letter* 143 (1992) 69–73; Burnett, et al., *J. Urol.* 150.1 (1993) 73–6; Burnett, et al., *Science* 257.5068 (1992) 401–3) localizing NOS to the autonomic nerves of rat and human penis by both immunohistochemistry with rat cNOS antibody and by NADPH diaphorase histochemistry. The mechanism of action of NO$^-$ is thought to be as follows: after production, NO$^-$, a highly lipophilic substance, quickly diffuses (in three dimensions (Christ, et al., *Biophysical Journal* 67:1335–1344 (1994)) into corporal smooth muscle cells, where it results in activation of soluble guanylate cyclase, catalyzing the conversion of GTP to cGMP. This increase in cGMP activates protein kinase G, which, as illustrated in FIG. 2, leads to decreases in intracellular Ca$^{2+}$, producing corporal smooth muscle relaxation (Moncada, S., *Acta Physiol Scand* 145 (1992) 201–227). As mentioned above, there is also recent evidence that in at least some vascular smooth muscle cells, NO_ may directly interact with K channels to elicit hyperpolarization and smooth muscle relaxation.

In the flaccid state NOS activity is thought to be minimal (Ignarro, et al., *Biochem Biophys Res Commun* 170 (1990) 843–850; Rajfer, et al., *New England Journal of Medicine* 326 (1992) 90–94; Azadozi, et al., *J. Urol.* 147.1 (1992) 220–225; Brock, et al., *Urology* 42.3 (1993) 412–417; Hellstrom, et al., *J. Urol.* 151.6 (1994) 1723–7; Pickard, et al., *British Journal of Urology* 75.4 (1995) 516–22; Carrier, et al., *J. Urol.* 153.5 (1995) 1722–7; Garban, et al., *American Journal of Physiology* (1995) H467–H475; Burnett, et al., *Biology of Reproduction* 52.3 (1995) 485–9). The intensity of the histochemical detection of NADPH diaphorase in cavernosal tissue has been shown to be decreased in patients with cavernosal nerve injury, implying decreased NOS activity (Brock, et al., *Urology* 42.3 (1993) 412–417). Furthermore, it has been suggested that the impaired relaxation responses (to electric field stimulation) of the cavernosal nerve of diabetic men may also be due to decreased NOS production (Saenz de Tejada, I., *New England Journal of Medicine* 320.16 (1989) 1025–30; Taub, et al., *Urology* 42 (1993) 698; Christ, G. J., *Urologic Clinics of North America* 4 22.4 (1995) 727–745; Vernet, et al., *Endocrinology* 136 (1995) 5709–5717). Thus, the introduction of a constitutively expressed cDNA for nitric oxide synthase might be expected to result in corporal smooth muscle relaxation and greater resting and nerve-stimulated pressure responses. As described below, the cDNA for neuronal NOS has been inserted into the corpus cavernosa of rats and a statistically significant, and physiologically relevant alteration was observed in the intracavernous pressure response to electrical stimulation of the cavernous nerve (Table 2).

Selection of Rat model. Rat was selected for the gene therapy studies, as the rat penis has been shown to be histologically and pharmacologically similar to human penis (Lesson, et al., *Investigative Urology* 3.2 (1965) 144–145). Among many known models, the rat is excellent for the study of penile erection (Lesson, et al., *Investigative Urology* 3.2 (1965) 144–145; Quinlan, et al., *J. Urol.* 141.3 (1989) 656–61; Chen, et al., *J. Urol.* 147 (1992) 1124–1128; Martinez-Pineiro, et al., *European Urology*, 25 (1994) 62–70) neurogenic and diabetic impotence (Rehman, et al., *Am J Physiol* (1997) in press).

MAXI-K CHANNEL RESULTS

Evidence that K Channels Modulate Corporal Smooth Muscle Relaxation: The putative role of the maxi-K channel in mediating NTG-and PGE$_1$-induced relaxation responses in the human corpora. Evidence from both cellular and isolated tissue studies documents the important role of the maxi-K channel in modulating relaxation responses in this tissue.

Figure 1:
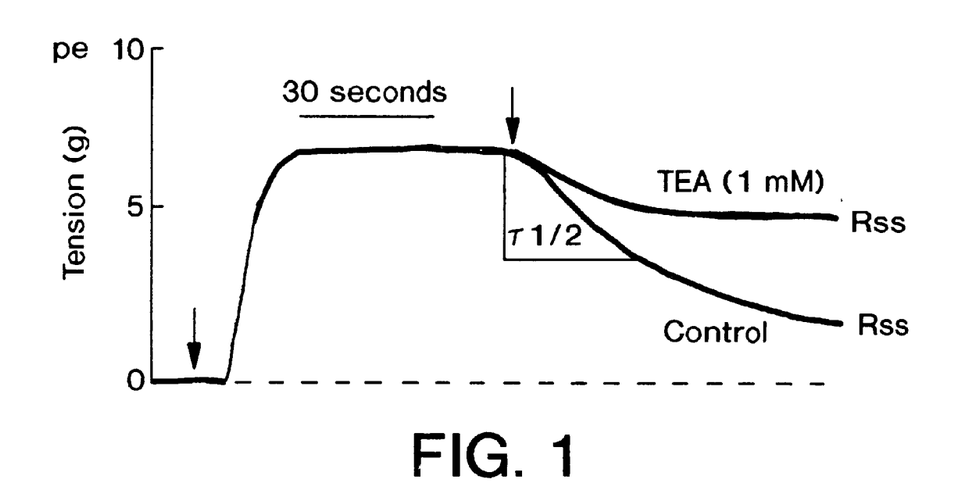
FIG. 1 illustrates how selective blockade of the maxi-K channel alters the NTG-induced relaxation response in isolated human corporal tissue strips. A modification of a previously published kinetic protocol was used (Christ, et al., *American Journal of Physiology* 263: H15–H19 (1992)) to derive two parameters; $\tau_{1/2}$:the time elapsed from addition of NTG to achievement of 50% of the steady-state relaxation response; RSS: the steady-state magnitude of the NTG-induced relaxation response. Note that preincubation of isolated corporal tissue strips resulted in a significant reduction in the magnitude of the NTG-induced relaxation response (100 nM). PE=Phenylephrine; NTG=Nitroglycerine.

NTG & maxi-K: As illustrated by the representative example in FIG. 1, in addition to the aforementioned effects on PE-induced contractile responses, selective blockade of the maxi-K channel with 1 mM TEA also results in a significant attenuation of the NTG-induced relaxation response (100 nM). Studies on five other corporal tissue strips revealed that the mean ±S.E.M. % relaxation response elicited by 100 nM NTG was of 20.3±3.2%; compare this value with the expected value of 50.1%, as determined in another recent publication. This finding documents that activation of the maxi-K channel is also likely to be an important component of the NTG-induced relaxation response. Consistent with this hypothesis, preliminary patch clamp studies cells (i.e., attached patch recording mode) on cultured corporal smooth muscle cells, with albeit much greater NTG concentrations (100 μM), demonstrated an NTG-induced increase in maxi-K channel activity to cultured corporal smooth muscle.

PGE$_1$ & maxi-K: Recent electrophysiological studies utilizing all four recording modes documented that PGE$_1$ causes a concentration-dependent increase in the activity of the maxi-K channel; over the same concentration range as we observe cAMP formation in cultured cells and relaxation of precontracted isolated human corporal smooth muscle strips (Zhang, et al., *J. Urol.* 155:678A (1996)). In addition, this increase in maxi-K channel activity is correlated with significant alterations in the ET-1-induced intracellular calcium transient seen in fura-2 loaded cultured corporal smooth muscle cells. Specifically, preincubation of cultured human corporal smooth muscle cells with 500 nM PGE$_1$ resulted in a significant ≈40% decrease in the peak amplitude of the ET-1-induced (50 nM) calcium transient above baseline (i.e., ≈70 nM) from a control value of 161.5±19.5 nM to 102.6±9.5 nM (Zhao, et al., *J. Urol.* 155:678A (1996)). Note that this decrease is indistinguishable from the decrease seen in absence of extracellular Ca$^{2+}$ (2 mM EGTA) or when cells are preincubated with nifedipine (Zhao & Christ, *J. Urol.* 154:1571–1579 (1995)) (or verapamil (Christ et al., unpublished observations); both of which are blockers of the L-type voltage-dependent calcium channel).

human smooth muscle maxi-K cDNA, hSlo, results in a significant decrease (≈25%) in the mean resting intracellular calcium levels, as well as a decrease (≈45%) in the peak amplitude of the ET-1-induced intracellular calcium transient. While the physiological significance of the former observation is uncertain, note, that the effects of transfection on the ET-1-induced intracellular calcium transient (Table 5), are remarkably similar to those seen in the presence of PGE$_1$, nifedipine and verapamil, or in the absence of extracellular calcium. Taken together, all of these data are totally consistent with the hypothesis that increased maxi-K channel activity, following either the presence of a greater number of maxi-K channels (presumably the effect of the transfection, although this has not yet been unequivocally established), or following cellular activation with, for example, PGE$_1$, is associated with cellular hyperpolarization, decreased transmembrane calcium flux through L-type voltage-dependent calcium channels, and a corresponding decrease in the peak amplitude of the ET-1-induced calcium transient. Moreover, since the peak amplitude of the intracellular calcium transient measured on cultured corporal smooth muscle cells accurately tracks the magnitude of the steady-state contractile response measured on isolated corporal tissue strips (Christ, et al., *J. Urol.* 153:1998–2003 (1995)), these data provide compelling evidence that the increased activity of the maxi-K channel modulates the magnitude of the corporal smooth muscle contractile response, at least in part, by altering transmembrane calcium flux. It is important to point out that the dual role of the maxi-K channel in modulating both the magnitude of contraction and relaxation takes advantage of the fact that maxi-K-induced inhibition of transmembrane calcium flux can occur following agonist (PE or ET-1)-induced increases in intracellular calcium, or following PGE$_1$-(presumably PKA) or NTG-induced (presumably PKG) increases in phosphorylation of the maxi-K channel; these ideas are consistent with the literature in other vascular smooth muscle cell types (see Table 5, below, and FIG. 2).

TABLE 4

Summary of Documented in vitro effects of the maxi-K channel on the physiology of corporal smooth muscle

| PE-induced contraction increased | Resting corporal smooth muscle tone increased | Resting intracellular calcium levels decreased | ET-1-induced calcium response decreased | Relaxation response decreased | Channel Activity increased |
|---|---|---|---|---|---|
| YES (1 mM TEA) | YES (10–100 mM TEA) | YES transfection with (hSlo cDNA) | YES transfection with (hSlo cDNA) or preincubation with PGE$_1$ (500 nM) | YES (1 mM TEA) | YES 100 μM NTG or 30 nM–30 μM PGE$_1$ |

Finally, it is herein shown (Table 6) that transfection of cultured human corporal smooth muscle cells with the

TABLE 5

Effects of vasoactive compounds on ion channel activity, membrane potential and corporal smooth muscle tone Membrane Potential
−30 mV
(DEPOLARIZED; i.e., Contracted)

| Agonist | Channel Type Affected | Putative Mechanism | Effect on Smooth Muscle Tone |
|---|---|---|---|
| ET-1 | L-type Ca$^{2+}$ increases | voltage or phosphorylation | increased tone |
| PE | K$_{Ca}$ increases | Ca$^{2+}$-sensitive | modulates increase in tone |
| KCl | K$_{ATP}$ increases | decreased ATP | modulates increase in tone |
| TEA | K$_{Ca}$ decreases | channel blockade | increased tone |
| Glibenclamide | K$_{ATP}$ decreases | channel blockade | increased tone |

↑
−40 to −50 mV
(RESTING POTENTIAL)
↓

| PGE$_1$ | K$_{Ca}$ increases | phosphorylation | decreased tone |
| NTG | L-type Ca$^{2+}$ decreases | voltage or phosphorylation | decreased tone |
| PINACIDIL | K$_{ATP}$ increases | increased mean open time | decreased tone |

TABLE 5-continued

Effects of vasoactive compounds on ion channel activity, membrane potential and corporal smooth muscle tone Membrane Potential
−30 mV
(DEPOLARIZED; i.e., Contracted)

| Agonist | Channel Type Affected | Putative Mechanism | Effect on Smooth Muscle Tone |
|---|---|---|---|

Membrane Potential
−60 mV
(HYPERPOLARIZED; i.e., Relaxed)

TABLE 6

Effect of transfection with hSlo cDNA on resting and ET-1-induced changes in $Ca_i$.

| Control Cells (n = 17) | | TT Transfected Cells (n = 32) | |
|---|---|---|---|
| Resting $Ca_i$ | ET-1 (50 nM) | Resting $Ca_i$ | ET-1 (50 nM) |
| 74.7 ± 4.0 nM | 164.1 ± 17.8 nM | *56.7 ± 2.5 nM | *90.8 ± 6.6 nM |

*-denotes a statistically significant difference from control values; $p < 0.001$, Student's t test for unpaired samples. $Ca_i$ refers to the intracellular calcium concentrations. The values given for the ET-1 induced increase represent the peak amplitude of the intracellular calcium transient as described in Zhao & Christ, J. Urol. 154 (1995) 1571–1579.

As a first test of the potential utility of modulating K channel activity to the therapy of erectile dysfunction, preliminary studies were conducted on a rat model in vivo. Briefly, it was found that injection of naked cDNA encoding the human smooth muscle maxi-K channel (i.e., hSlo; obtained from Dr. Salkoff, Washington University), into the rat corpora, resulted in significant uptake and gene expression. This was documented by the fact that the nerve-stimulated intracavernous pressure increases observed on 8 month old Sprague-Dawley rats injected with the maxi-K cDNA were significantly greater than the intracavernous pressure responses seen in age-matched control, sham-operated animals (FIG. 3 and Table 5). Moreover, the incorporation of this gene (again, as judged by the significant elevation of intracavernous pressure relative to control animals) remained stable for more than three months. These in vivo studies are entirely consistent with all of the in vitro observations made by the inventors, and thus, further document the importance of K channels to the modulation of corporal smooth muscle tone. Finally, although it is recognized that there may be other subunits of the human smooth muscle maxi-K channel in human corporal tissue (L. Salkoff, personal communication), these studies represent a reasonable starting point for evaluating the role of the maxi-K channel to erectile physiology. In summary, these studies appear to provide hope that, after obtaining a more detailed understanding of how K channels modulate smooth muscle tone in a diverse patient population, one might use the powerful tools of molecular genetics to more precisely alter the balance between contraction and relaxation; such that men would be able to more consistently obtain rigid erections on their own, without the necessity of resorting to any of the limitations associated with current therapeutic regimens.

What is claimed is:

1. A method for inducing penile erection in a subject comprising the introduction and expression of a DNA sequence encoding a maxi-K potassium channel protein into a sufficient number of penile cells of the subject to induce penile erection in the subject.

2. The method of claim 1, wherein the cell is a corporal smooth muscle cell or an arterial smooth muscle cell.

3. The method of claim 1, wherein the DNA sequence is introduced by naked DNA transfer.

4. The method of claim 1, wherein the DNA sequence is genomic DNA or cDNA.

5. The method of claim 1, wherein the subject has erectile dysfunction.

6. The method of claim 5, wherein the erectile dysfunction results from incomplete relaxation of smooth muscle.

7. The method of claim 5, wherein the erectile dysfunction results from neurogenic dysfunction.

8. The method of claim 5, wherein the erectile dysfunction results from arteriogenic dysfunction.

9. The method of claim 5, wherein the erectile dysfunction results from veno-occlusive dysfunction.

* * * * *